United States Patent [19]
Spohn et al.

[11] Patent Number: 5,060,503
[45] Date of Patent: Oct. 29, 1991

[54] TEST KIT FOR GAS DETECTORS

[75] Inventors: William P. Spohn, Swissvale; Richard M. Hickox, Ross Township, Allegheny County, both of Pa.

[73] Assignee: Bacharach, Inc., Pittsburgh, Pa.

[21] Appl. No.: 477,033

[22] Filed: Feb. 8, 1990

[51] Int. Cl.$^5$ .............................................. G01D 18/00
[52] U.S. Cl. ...................................................... 73/1 G
[58] Field of Search ......................................... 73/1 G

[56] References Cited

U.S. PATENT DOCUMENTS

| 3,180,132 | 4/1985 | Robinson et al. | 73/1 G |
| 3,242,715 | 3/1966 | Hübner | 73/1 G |
| 3,693,401 | 9/1972 | Purt et al. | 73/1 G |
| 3,817,108 | 6/1974 | Principe et al. | 73/1 G X |
| 3,951,855 | 4/1976 | Principe et al. | 73/1 G X |
| 4,287,750 | 9/1981 | Eckstein et al. | 73/1 G |
| 4,301,674 | 11/1981 | Haines et al. | 73/1 G |
| 4,322,964 | 4/1982 | Melgaard et al. | 73/1 G |
| 4,460,448 | 7/1984 | Wolcott | 204/266 |
| 4,462,244 | 7/1984 | Lee | 73/1 G |
| 4,715,985 | 12/1987 | Peon et al. | 73/1 G X |
| 4,722,217 | 2/1988 | Arnett et al. | 73/1 G |
| 4,723,436 | 2/1988 | Moreth et al. | 73/1 G |
| 4,882,576 | 11/1989 | Boyd | 73/1 G X |
| 4,967,958 | 11/1990 | Helsper et al. | 73/1 G X |

Primary Examiner—Tom Noland
Attorney, Agent, or Firm—Webb, Burden, Ziesenheim & Webb

[57] ABSTRACT

A test kit for gas detectors is disclosed, including an aerosol can containing a predetermined gas mixture of predetermined concentration and a pierceable conduit having first and second open ends, the first open end being adapted to engage an inlet opening of the gas detector. The pierceable conduit further includes a plug having an orifice therethrough for admitting small amounts of air into an interior of the conduit. The plug is located in the conduit adjacent the second open end. A hollow needle is adapted to engage an outlet valve on the aerosol can, and the needle is manipulated to pierce the conduit, delivering the predetermined gas mixture of predetermined concentration to the gas detector.

15 Claims, 2 Drawing Sheets

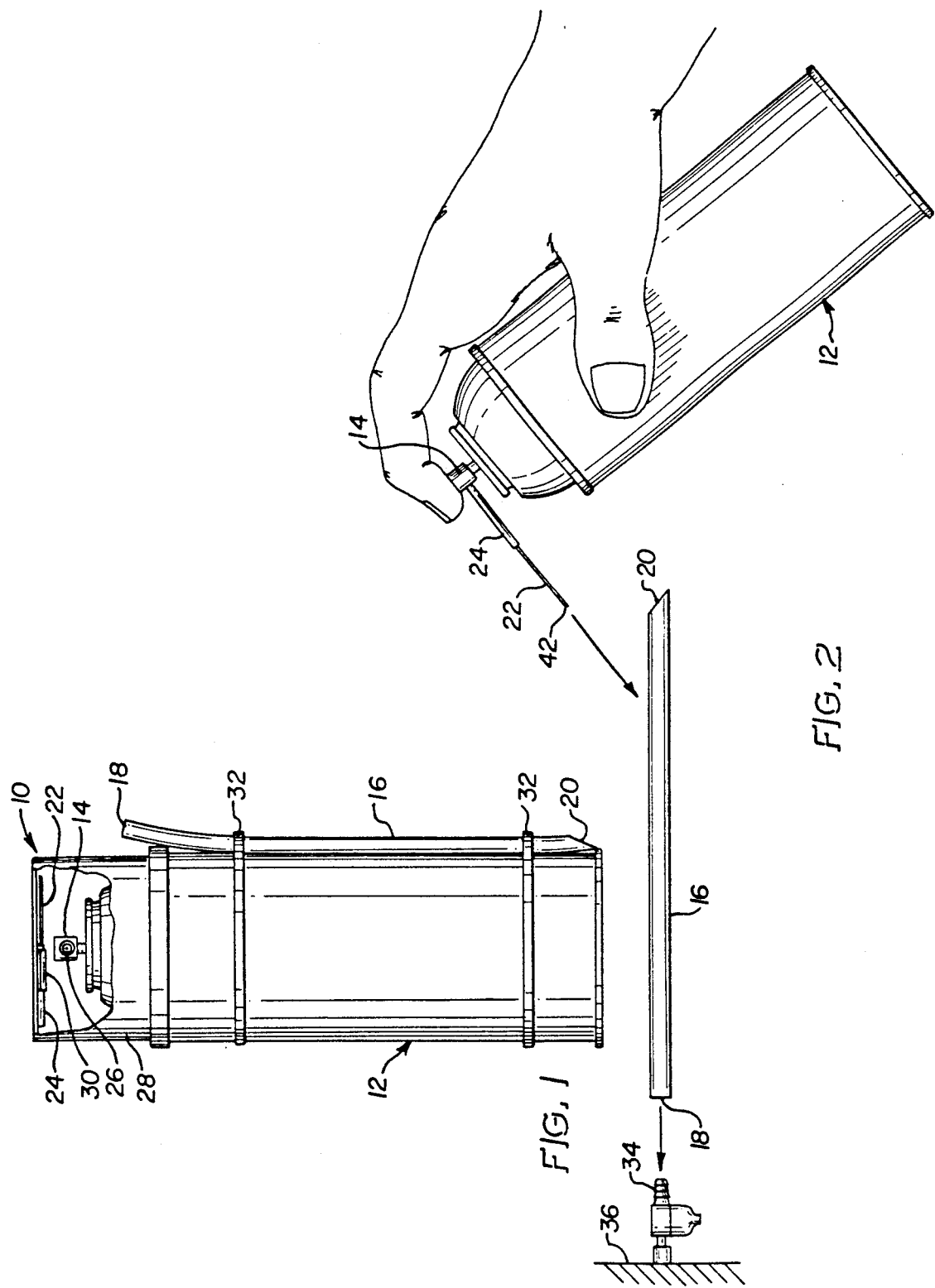

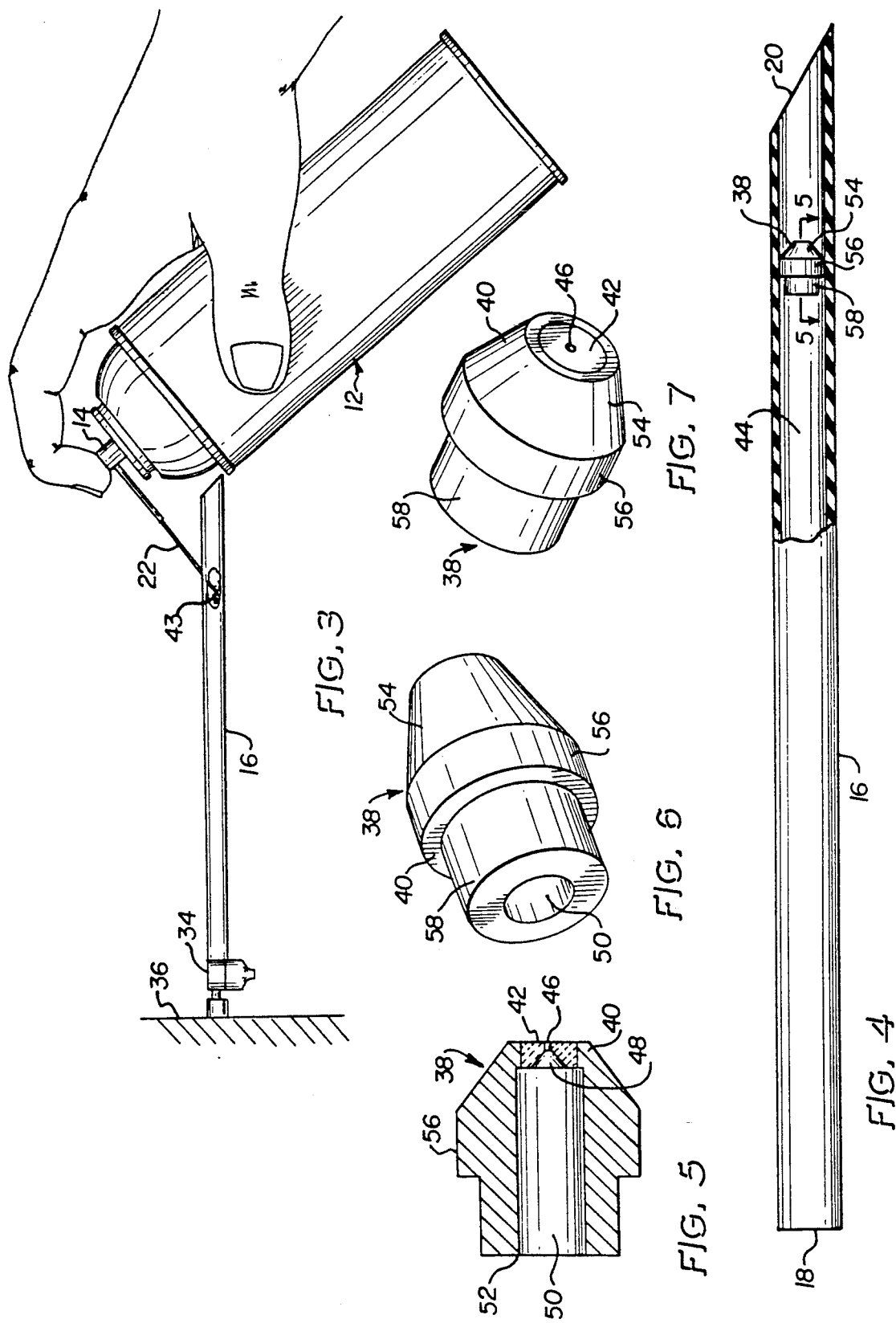

TEST KIT FOR GAS DETECTORS

BACKGROUND OF THE INVENTION

1. Field of the Invention

This invention relates to the calibration of instruments used to detect or monitor gas and, more particularly, to methods and devices for easily, quickly and inexpensively testing the calibration of a gas detector.

2. Description of the Prior Art

Gas detectors are known to become inaccurate through use or the passage of time, or both. It is a common practice to adjust the instrument so as to maintain accurate sensitivity. Typically, a test gas of known composition is passed through the gas detector to determine whether the reading developed by the instrument accurately reflects the composition of the test gas. Full calibration procedures must be undertaken periodically to assure accuracy of the instrument. However, it is frequently desirable to make a cursory check of the instrument's operation without going through the full effort and expense involved in formal calibration procedures.

Presently, there exists no known, low cost and effective method for performing both intermediate and full calibration procedures on sophisticated gas detectors. A typical calibration kit for such instruments, including a regulator, valving, a large air cylinder and a flowmeter, can cost up to $350.00. The user incurs a tremendous expense just to determine if the instrument is working properly. See, for example, U.S. Pat. No. 4,723,436. Other arrangements are shown in U.S. Pat. Nos. 4,287,750, 4,322,964 and 4,460,448.

Previous attempts have been made to devise simple, manageable systems for calibrating gas detectors. One such apparatus is disclosed in U.S. Pat. No. 4,722,217 to Arnett et al., which focuses on calibration of gas detectors used in systems delivering anesthesia to hospital patients. The Arnett et al. patent discloses a calibration test gas container connected by tubing to the inlet of a gas detector. The valve on the container is manipulated, along with the detector's pumping means, to stall a test gas within the detector, exposing the gas to the detector's sensor. Distensible container means are also disclosed for use in avoiding over-pressurization of the gas detector system.

U.S. Pat. No. 4,462,244 to Lee discloses an apparatus for field testing smoke detectors. A drum-like container is provided with an air impeller and carries therein an aerosol can of smoke simulation material. The air impeller, the spray can, and a movable wand are manipulated to direct smoke to the detector's sensor.

While each of these devices is portable, they are too complicated in construction and application to be useful for conducting cursory calibrations of gas detectors. In some circumstances, they may even prove undesirably complicated or expensive for use in full calibration procedures.

Accordingly, it is an object of the present invention to provide an inexpensive, simply operated, easily manageable kit for conducting both cursory and full calibration procedures on gas detectors.

SUMMARY OF THE INVENTION

Accordingly, we have invented a test kit for gas detectors which includes an aerosol can which contains a predetermined gas mixture of predetermined concentration and which is equipped with an outlet valve. The test kit also includes a pierceable conduit with first and second open ends, the first end adapted to be positioned on an inlet opening of a gas detector and the second end having a plug inserted in the conduit adjacent thereto. The plug has an orifice extending therethrough which is in communication with an interior of the conduit. A hollow needle is also provided which is attachable to the outlet valve on the aerosol can and which is adapted to pierce the conduit and transfer gas from the can into the interior of the conduit when the first open end of the conduit is positioned on the inlet opening of the gas detector.

The test kit may also include a lid secured to the aerosol can and holding the hollow needle when the needle is not attached to the outlet valve of the aerosol can. Further, the test kit may include an indicator or marking on the pierceable conduit for designating which end of the pierceable conduit is to be positioned on the inlet opening of the gas detector. In a preferred embodiment, the first end of the conduit has a flat profile and the second end has an angled profile. The plug may include a housing having a jewelled material with an aperture therethrough. The pierceable conduit may be removeably attached to the aerosol can.

A method using this test kit is also disclosed.

Other features and advantages of the present invention will become apparent from the following detailed description in conjunction with the accompanying drawings.

BRIEF DESCRIPTION OF THE DRAWINGS

FIG. 1 is a side elevational view, partially in section, of a test kit for gas detectors in accordance with the present invention;

FIG. 2 is a side elevational view showing the test kit of FIG. 1 being installed on a gas detector;

FIG. 3 is a side elevational view, partially in section, showing the test kit of FIG. 1 installed on a gas detector;

FIG. 4 is a side elevational view, partly in section, of a pierceable conduit included in the test kit of FIG. 1;

FIG. 5 is a section taken through the plug in the pierceable conduit along lines 5—5 of FIG. 4;

FIG. 6 is a perspective view of the plug shown in FIG. 4; and

FIG. 7 is a perspective view, from another angle, of the plug shown in FIG. 4.

DETAILED DESCRIPTION OF THE PREFERRED EMBODIMENT

One embodiment of the test kit 10 for gas detectors in accordance with the present invention is shown in FIG. 1 in its packaged state. The test kit 10 includes an aerosol can 12 which has an outlet valve 14 thereon. The aerosol can 12 contains a predetermined gas mixture of predetermined concentration, such as 750 parts per million carbon monoxide in nitrogen. Variations with other gases and different concentrations are virtually limitless. The particular gas mixture and concentration utilized depends upon the nature of the gas detector being tested.

The test kit 10 also includes a pierceable conduit 16 which has a first open end 18 and a second open end 20. The first open end 18 has a profile which is generally flat, i.e., perpendicular to the longitudinal axis of the pierceable conduit 16, and the second open end 20 has a profile which is angled with respect to the longitudinal axis. The significance of these different profiles will be discussed below. In the preferred embodiment, the pierceable conduit 16 is constructed of neoprene, which provides the resiliency required to allow the present invention to be used several times. The pierceable conduit 16 may be constructed of various other materials, as long as those materials are penetrable with sharp objects, yet resilient, so that puncture holes of small diameter will effectively be self-sealed on extraction of the object from the conduit.

The test kit 10 further includes a hollow needle 22 which is equipped with a fitting 24. The fitting 24 is adapted to engage a nozzle 26 on the outlet valve 14 so that gas may be expelled from the aerosol can 12 through the hollow needle 22 when the outlet valve 14 is opened.

When the hollow needle 22 is not engaged to the nozzle 26, it may be carried on a lid 28 which is secureable to the aerosol can 12. FIG. 1 shows the hollow needle 22 removeably attached to the inside of the lid 28 with a length of adhesive tape 30. The pierceable conduit 16 is shown removeably attached to the aerosol can 12 by rubber bands 32. Other devices for removeably attaching the conduit 16 and needle 22 may be utilized, such as VELCRO ®, u-clips, clamps, alligator ties and the like.

FIG. 2 shows the initial steps required for practicing the test kit 10 shown in FIG. 1. The pierceable conduit 16 is removed from the aerosol can 12 and positioned on an inlet opening 34 of a gas detector 36. Here, the differing profiles of the first open end 18 and the second open end 20 become important. The profile of the first open end 18 indicates to the user that this end must be positioned on the inlet opening 34. It will be appreciated by those skilled in the art that various other forms of indicating proper orientation of the pierceable conduit 16 may be utilized, including color codes, tabs, different textures, and the like.

Referring to FIG. 4, a plug 38 is positioned within the pierceable conduit 16 adjacent the second open end 20. The major portion of the pierceable conduit 16 should be intermediate of the inlet opening 34 and the plug 38. As will be described in more detail below, the plug 38 includes an orifice therethrough which admits a small amount of air through the plug 38 and into the pierceable conduit 16.

Referring once again to FIG. 2, the hollow needle 22 is removed from the lid 28 and is engaged to the nozzle 26 on the outlet valve 14 via the fitting 24. A pumping device (not shown) in the gas detector 36 is then engaged to draw air through the orifice of the plug 38, through the pierceable conduit 16 and into the inlet opening 34 of the gas detector 36. As shown in FIG. 3, the hollow needle 22 is then manipulated to pierce the conduit 16, placing a tip 43 of the hollow needle 22 inside the conduit 16 at a location intermediate of the plug 38 and the inlet opening 34. Specifically, the hollow needle 22 should pierce the conduit 16 at least two inches from the second open end 20 to insure that the tip 43 is in an area of reduced pressure caused by the combined actions of the pump inside the gas detector 36 and the orifice in the plug 38.

Once the tip 43 of the hollow needle 22 is in place within the pierceable conduit 16, the outlet valve 14 is opened and the predetermined gas mixture of predetermined concentration is transferred from the aerosol can 12 through the hollow needle 22 and into the pierceable conduit 16. The gas detector 36 is then monitored to determine if it accurately reads the concentration of the gas in the aerosol container 12, or at least develops a reading close to that concentration. After sufficient gas has been introduced into the gas detector 36 to complete the desired test, the outlet valve 14 is closed, the pumping device is disengaged, the hollow needle 22 is removed from the pierceable conduit 16, the conduit 16 is removed from the inlet opening 34 and the test kit 10 is reassembled as shown in FIG. 1.

The plug 38 is shown in detail in FIG. 4 through FIG. 7. The plug 38 includes a housing 40 containing a jewelled material 42 at one end thereof. The housing 40 may be fashioned from metal, such as brass, or resilient plastic long as it allows the plug 38 to be snugly fit in an interior 44 of the pierceable conduit 16. The jewelled material 42 may be an industrial jewel, such as synthetic sapphire, but other materials may be utilized as long as they are readily cut to a precise dimension and can have small diameter holes formed therethrough. The plug 38 is inserted into the pierceable conduit 16 at the second open end 20 by hand, pinching the pierceable conduit 16 to force the plug 38 towards the first open end 18. The jewelled material 42 includes therethrough an aperture 46 and a flare 48 as shown in FIG. 5. The flare 48 is oriented toward a cylindrical portion 50 in the housing 40 which continues to the rear terminus 52 of the plug 38. The aperture 46, flare 48 and cylindrical portion 50 together form an orifice through the plug 38. The housing 40 includes a frusto-conical section 54 whose base diameter coincides with a first cylindrical section 56, which is intermediate of the frusto-conical section 54 and a second cylindrical section 58 of lesser diameter. The jewelled material 42 is preferably located in the end of the plug 38 including the frusto-conical section.

In operation, ambient air is drawn first through the aperture 46, then through the flare 48 and finally out of the plug 38 through the cylindrical portion 50 and into the interior 44 of the pierceable conduit 16. The ultimate effect derived from placement of the plug 38 having an orifice therethrough inside the pierceable conduit 16 is creation of a steady state flow condition in the pierceable conduit 16 when a vacuum is drawn thereon. This condition prevents the pumping device in the gas detector 36 from drawing a complete vacuum on the pierceable conduit 16 while at the same time preventing undue dilution of the test gas sample by admitting only a minimal amount of ambient air into the pierceable conduit 16.

As shown in FIG. 1, the present invention may be embodied in a test kit 10 for conveniently and inexpensively carrying out both intermediate and expanded calibration procedures on gas detectors. The components of the test kit 10 may be removably attached to one another by various means to form a compact arrangement which permits the test kit 10 to be conveniently handled, stored and reused at a later date. Additionally, the aerosol can 12 can be disposed when empty. Conventional cylinders must usually be returned for refill. The simple design of the test kit 10 allows it to be used and reused with various types of gases in both cursory checks and full calibrations of gas detectors.

The test kit 10 of the present invention is relatively inexpensive to manufacture since it can be made substantially of commercially available parts. For example, a suitable aerosol can, including a hollow needle, may be obtained from Scott Specialty Gases, Plumsteadville, Pennsylvania. Additionally, a suitable plug having a jewelled material and orifice therethrough may be obtained from Aurele M. Gatti, Inc. of Trenton, New Jersey.

The plug 38 having an orifice therethrough allows the user to easily make use of the gas detector's pumping device for delivering test gas to the gas detector. The pierceable conduit 16 and the hollow needle 22 provide easily manageable conduit means which may endure multiple uses in providing substantially contamination-free communication between the aerosol can 12 and the gas detector 36. Additionally, these component parts may be shrink-wrapped by the manufacturer in cellophane or the like for ease of handling, storage and marketing.

While a particular form of the test kit has been illustrated and described, it will be apparent to those skilled in the art that various modifications of the kit can be made within the appended claims.

We claim:

1. A test kit for gas detectors comprising:
   an aerosol can containing therein a predetermined gas mixture having a predetermined concentration, said can having an outlet valve thereon;
   a pierceable conduit having first and second open ends, with said first open end adapted to be positioned on an inlet opening of a gas detector and with said conduit having a plug positioned therein adjacent said second open end, with said plug having an orifice extending therethrough and communicating with an interior of said conduit; and
   a hollow needle attachable to said outlet valve and adapted to pierce said conduit and transfer gas from said can into the interior of said conduit when the first open end of said conduit is positioned on the inlet opening of the gas detector.

2. The test kit according to claim 1 further including a lid secureable to said aerosol can and adapted to carry said hollow needle when the hollow needle is not attached to said outlet valve.

3. The test kit according to claim 1 wherein said pierceable conduit further includes means for indicating which end of the conduit is to be positioned on the inlet opening of the gas detector.

4. The test kit according to claim 3 wherein said first end of said pierceable conduit has a profile which is flat and said second end of said pierceable conduit has a profile which is angled.

5. The test kit according to claim 1 wherein said plug includes a housing having a jewelled material with an aperture therethrough for admitting small amounts of air into an interior of the conduit.

6. The test kit according to claim 1 further including means for removably attaching the pierceable conduit to the aerosol can.

7. A test kit for as detectors comprising:
   an aerosol can containing therein a predetermined gas mixture 4 having a predetermined concentration, said can having an outlet valve thereon;
   a pierceable conduit having first and second open ends, with said first open end adapted to be positioned on an inlet opening of a gas detector and with said conduit having a plug positioned therein adjacent said second open end, with said plug having an orifice extending therethrough in communication with an interior of said conduit.
   a hollow needle attachable to said outlet valve and adapted to pierce said conduit and transfer gas from said aerosol can into the interior of the conduit when the first open end of the conduit is positioned on the inlet opening of the gas detector; and
   means for removably attaching said pierceable conduit to the aerosol can.

8. The test kit according to claim 7 further including a lid which may be secured to said aerosol can and which may be adapted to carry said hollow needle when the hollow needle is not attached to said outlet valve.

9. The test kit according to claim 7 wherein said pierceable conduit further includes means for indicating which end of the conduit is to be positioned on the inlet opening of the gas detector.

10. The test kit according to claim 9 wherein said first end of said pierceable conduit has a profile which is flat and said second end of said pierceable conduit has a profile which is angled.

11. The test kit according to claim 7 wherein said plug further comprises a housing having a jewelled material with an aperture therethrough for admission of small amounts of air into the interior of the conduit.

12. A test kit for gas detectors comprising:
   an aerosol can containing therein a predetermined gas mixture having a predetermined concentration, said can having an outlet valve thereon;
   a pierceable conduit having first and second open ends, with said first open end adapted to be positioned on an inlet opening of a gas detector and with said conduit having a plug positioned therein adjacent said second open end, with said plug having an orifice extending therethrough in communication with an interior of said conduit;
   said plug further comprising a housing having a jewelled material with an aperture therethrough for admitting small amounts of air into the interior of said conduit;
   a hollow needle attachable to said outlet valve and adapted to pierce said conduit and transfer gas from said aerosol can into the interior of the conduit when the first open end of the conduit is positioned on the inlet opening of the gas detector; and
   means for removably attaching the pierceable conduit to the aerosol can.

13. The test kit according to claim 12 further including a lid which is securable to said aerosol can and adapted to carry said hollow needle when the hollow needle is not attached to said outlet valve.

14. The test kit according to claim 12 wherein said pierceable conduit further includes means for indicating which end of the conduit is to be positioned on the inlet opening of the gas detector.

15. The test kit according to claim 14 wherein said first end of said pierceable conduit has a profile which is flat and said second end of said pierceable conduit has a profile which is angled.

* * * * *

UNITED STATES PATENT AND TRADEMARK OFFICE
CERTIFICATE OF CORRECTION

PATENT NO. : 5,060,503

DATED : October 29, 1991

INVENTOR(S) : William P. Spohn, and Richard M. Hickox

It is certified that error appears in the above-identified patent and that said Letters Patent is hereby corrected as shown below:

Column 4 Line 13 after "plastic" insert --, as--.

Claim 7 Line 54 Column 5 "as" should read --gas--.

Claim 7 Line 56 Column 5 after "mixture" delete --4--.

Claim 7 Line 2 Column 6 "conduit." should read --conduit;--.

Signed and Sealed this

Twenty-third Day of March, 1993

Attest:

STEPHEN G. KUNIN

*Attesting Officer*  *Acting Commissioner of Patents and Trademarks*